United States Patent
Georgi et al.

(10) Patent No.: US 12,220,677 B2
(45) Date of Patent: Feb. 11, 2025

(54) PROCESS FOR THE PREPARATION OF MICROCAPSULES

(71) Applicant: SYMRISE AG, Holzminden (DE)

(72) Inventors: Julian Alexander Georgi, Holzminden (DE); Benjamin Rost, Bodenwerder (DE); Diane Dröge, Bodenwerder (DE); Ralf Bertram, Holzminden (DE); Thorsten Böddeker, Brakel (DE)

(73) Assignee: SYMRISE AG, Holzminden (DE)

( * ) Notice: Subject to any disclaimer, the term of this patent is extended or adjusted under 35 U.S.C. 154(b) by 700 days.

(21) Appl. No.: 17/430,943

(22) PCT Filed: Feb. 13, 2019

(86) PCT No.: PCT/EP2019/053600
§ 371 (c)(1),
(2) Date: Aug. 13, 2021

(87) PCT Pub. No.: WO2020/164705
PCT Pub. Date: Aug. 20, 2020

(65) Prior Publication Data
US 2022/0105486 A1    Apr. 7, 2022

(51) Int. Cl.
| | |
|---|---|
| *B01J 13/14* | (2006.01) |
| *A61K 9/50* | (2006.01) |
| *B01J 13/20* | (2006.01) |
| *C11D 3/00* | (2006.01) |
| *C11D 3/50* | (2006.01) |

(52) U.S. Cl.
CPC ............ *B01J 13/14* (2013.01); *A61K 9/5031* (2013.01); *A61K 9/5089* (2013.01); *B01J 13/206* (2013.01); *C11D 3/001* (2013.01); *C11D 3/505* (2013.01); *C11D 2111/12* (2024.01)

(58) Field of Classification Search
CPC . A61K 8/87; A61K 8/062; A61K 8/11; A61K 8/345; A61K 8/41; A61K 8/732; A61K 8/88; A61K 9/5031; A61K 9/5089; A61K 2800/56; A61K 8/84; A61K 9/5026; A61K 9/5036; A61K 2800/10; A23P 10/30; A61Q 19/00; A61Q 13/00; A01N 25/28; B01J 13/206; B01J 13/16; B01J 13/14; B01J 13/22; C11D 3/505; C11D 17/0039; C11D 3/001; C11D 2111/12
See application file for complete search history.

(56) References Cited

U.S. PATENT DOCUMENTS

| | | | |
|---|---|---|---|
| 3,891,570 | A | 6/1975 | Fukushima et al. |
| 10,195,577 | B2 | 2/2019 | Burakowska-Meise et al. |
| 10,398,632 | B2 | 9/2019 | Aussant et al. |
| 10,835,885 | B2 | 11/2020 | Rost et al. |
| 2013/0089591 | A1 | 4/2013 | Vautrin et al. |
| 2013/0095158 | A1 | 4/2013 | Denuell et al. |
| 2013/0337023 | A1 | 12/2013 | Lei et al. |
| 2015/0252312 | A1 | 9/2015 | de Villeneuve et al. |
| 2017/0189283 | A1* | 7/2017 | Sasaki ............... C11D 3/505 |
| 2017/0252274 | A1* | 9/2017 | Lei ............... A61K 8/84 |
| 2018/0042825 | A1* | 2/2018 | Lei ............... A61K 8/84 |
| 2021/0238510 | A1 | 8/2021 | Ott et al. |

FOREIGN PATENT DOCUMENTS

| | | |
|---|---|---|
| DE | 2303866 A1 | 8/1973 |
| EP | 2669835 A1 | 12/2013 |
| EP | 3238816 A1 | 11/2017 |
| EP | 3300794 A2 | 4/2018 |
| JP | 2013-530979 A | 8/2013 |
| JP | 2013-537472 A | 10/2013 |
| JP | 2017-515661 A | 6/2017 |
| JP | 2017-533240 A | 11/2017 |
| JP | 2021-528226 A | 10/2021 |
| WO | WO-2008/098387 A1 | 8/2008 |
| WO | WO-2016/144798 A1 | 9/2016 |
| WO | WO-2017/058875 A1 | 4/2017 |
| WO | WO-2017/148504 A1 | 9/2017 |

OTHER PUBLICATIONS

Notice of Reasons for Refusal for Japanese Application No. 2021-547384, dated Sep. 2, 2022.
International Search Report and Written Opinion from International Application No. PCT/EP2019/053600 dated Oct. 22, 2019.

* cited by examiner

Primary Examiner — Lezah Roberts
Assistant Examiner — Abdulrahman Abbas
(74) Attorney, Agent, or Firm — MARSHALL, GERSTEIN & BORUN LLP

(57) ABSTRACT

The present invention relates to a process for the preparation of microcapsules, in particular isocyanate-based microcapsules with improved stability to carboxylic acid and aldehyde-containing active ingredients as core material. In addition, the present invention relates to microcapsules obtainable by the process according to the invention. In addition, the present invention relates to microcapsules, suspensions of such microcapsules, and the use of the microcapsules and suspensions as a component in detergents, fabric softeners, cleaning products, scent boosters (fragrance enhancers) in liquid or solid form, cosmetics, personal care products, agricultural products, or pharmaceutical products.

20 Claims, 5 Drawing Sheets

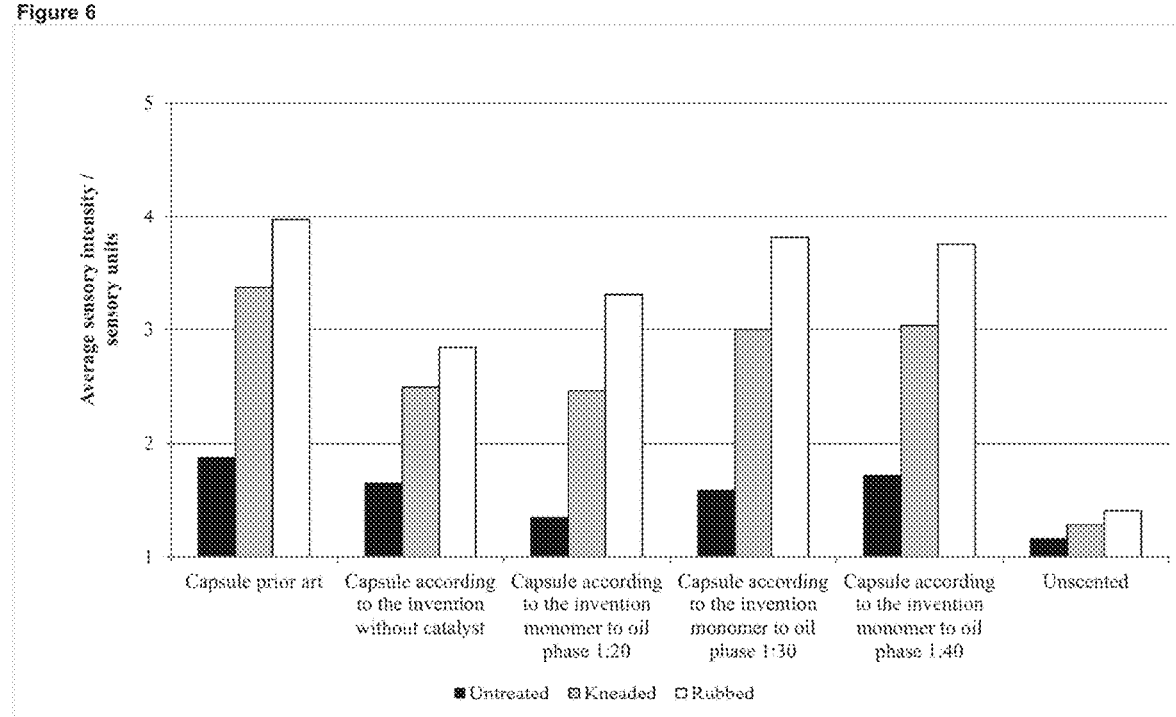

PROCESS FOR THE PREPARATION OF MICROCAPSULES

CROSS-REFERENCE TO RELATED APPLICATIONS

This is a U.S. National Phase of International Application No. PCT/EP2019/053600, filed Feb. 13, 2019, the contents of which are incorporated herein by reference.

FIELD OF INVENTION

The present invention relates to a process for the production of microcapsules, in particular isocyanate-based microcapsules, with improved stability to carboxylic acid, aldehyde and/or ester-containing active ingredients as core material. Furthermore, the present invention relates to microcapsules obtainable by the process according to the invention. In addition, the present invention relates to microcapsules, suspensions of such microcapsules, and the use of the microcapsules and suspensions as an ingredient in detergents, fabric softeners, cleaning products, scent boosters (fragrance enhancers) in liquid or solid form, cosmetics, personal care products, agricultural products, and pharmaceutical products.

The term "encapsulation" is generally understood by those skilled in the art to mean a technique by which finely dispersed solid, liquid or gaseous substances are surrounded by a film-forming shell of polymeric or inorganic wall materials and are thus immobilized. During manufacture, the polymers precipitate onto the substances to be encapsulated after emulsification and coacervation or interfacial polymerization. Encapsulation is thus a form of inclusion immobilization. The substances or active ingredients enclosed in the capsules are generally referred to as core material.

The aim here is to protect the active components known as active ingredients and to be able to release them in a targeted manner at a specific time. The active ingredients or active components often cannot be used directly for various reasons (for example, due to their solubility, reactivity, stability, etc.), or certain effects are to be achieved through microencapsulation (e.g. release curves for controlled release, unique selling propositions, etc.).

For diameters in the range of >100 μm, individual substance or active ingredient particles are coated using various spray technologies, while liquids are encapsulated using droplet processes.

Of particular interest are so-called microcapsules, which have diameters in the range of about 0.0001 to 5, preferably 0.001 to 0.5, and especially 0.005 to 0.1 mm.

For microcapsules with a diameter of less than 100 μm, however, encapsulation is only possible by depositing so-called wall formers at a phase interface. In the manufacturing process used industrially for this purpose, an emulsion or suspension of the hydrophobic core material in water is produced. The monomers present in the outer phase accumulate in a layer around the emulsion droplets or the dispersed solid particles of the core material and polymerize to form a compact shell. Depending on the wall material and the degree of crosslinking, individual properties of the microcapsules can thus be achieved.

In encapsulation, a distinction is made between: Matrix encapsulation: Here, the active ingredient(s) or active component(s) is/are homogeneously mixed with the shell component ("matrix") and a particle is formed in which the active ingredient(s) or active component(s) is/are uniformly distributed. Typically, the release determines either the diffusion of the active component(s) into the environment or the rate of degradation of the matrix. Core-shell encapsulation: the active ingredient(s) or active component(s) that form the core are encapsulated with a shell material. A true capsule with one or more shell(s) is formed. A rupture of the shell usually produces a complete release of the core material in a short time. However, it is also possible to produce an extremely slow release by the appropriate choice of shell.

Due to their properties, microcapsules are used in the printing industry, the food industry (vitamins, flavors, plant extracts, enzymes, microorganisms), agricultural chemistry (fertilizers, pesticides), the feed industry (minerals, vitamins, enzymes, pharmaceuticals, microorganisms), the pharmaceutical industry, the detergent industry, and the cosmetics industry, among others.

Encapsulation of an active ingredient with a suitable wall material (coating material) can be done for several reasons:
  Conversion of liquids into a manageable powder form (e.g. coating of vegetable oils, fats);
  time-controlled release of substances (dosage control, depot effect for pharmaceuticals, pesticides and fertilizers); Taste, odor and color coverage (e.g., bitter or spicy flavorings);
  Protection from light, oxidation, heat, acids or bases (e.g. vitamins, flavorings, etc.)
  Moisture protection (e.g. hygroscopic salts or minerals);
  Delay of losses of volatile components (e.g. aroma compounds); Prevention of premature chemical reactions with other mixture components;
  better handling before or during processing (flow properties, dust formation); Protection of personnel from harmful or unpleasant materials (chemicals, aroma concentrates); or
  better solubility/suspendability due to surface modification.

The contents of microcapsules can be released in various ways. Four typical mechanisms come into consideration:
  The capsules are mechanically destroyed by crushing or shearing. This mechanism is used, for example, with reaction carbonless paper.
  The capsules are destroyed by melting of the wall material. According to this mechanism, ingredients such as raising agents or flavors are released, for example, in baking mixtures only during the baking process.
  The capsules are destroyed by dissolving the wall material. This mechanism is used, for example, in washing powder so that encapsulated ingredients such as enzymes are only released during the washing process.
  The capsules remain intact, and the capsule contents are gradually released by diffusion through the capsule wall. According to this mechanism, for example, a slow and uniform release of drug substances in the body can be achieved.

Many articles of daily use, such as detergents, fabric softeners, washing powders, liquid detergents, shower gels, shampoos, deodorants, poly lotions, etc., are today perfumed with fragrances or fragrance mixtures. Very often, the fragrances interact with other components of the formulation, or the more volatile components of a perfume evaporate prematurely. This usually results in the fragrance impression of the perfume changing over time or even disappearing completely.

Microencapsulation of such fragrance mixtures offers the possibility of reducing or completely preventing interactions in the perfumed product or evaporation of the highly volatile fragrance components.

The microcapsules, which are both chemically and mechanically stable, are based, for example, on aminoplast resins, which are used as the wall or shell material. In addition to the high impermeability of the capsule shell, it is also very resistant to reactive chemicals. The production of these capsules is simplified by first preparing, under high shear and in the presence of emulsifiers, an O/W emulsion containing the water-soluble monomer, a so-called amine-formaldehyde precondensate, and the water-insoluble, hydrophobic active ingredient, such as a perfume oil. The polycondensation is initiated by a pH change, for example by adjusting the pH to about 3.5 by adding acid. The polycondensates deposit on the oil droplets in the emulsion and gradually envelop them. When the polycondensation is complete, the emulsion has become a microcapsule dispersion. However, the capsules still have a soft, elastic shell, which does not yet provide the necessary diffusion stability and texture properties. Therefore, a further step follows in which the temperature of the microcapsule dispersion is raised to about 60° C., which leads to crosslinking of the polymers in the wall and curing of the capsules. A corresponding process is known, for example, from EP 2 111 214 B1 (GIVAUDAN).

From DE 23 03 866 A1 (FUJI), a stable concentrated mixture for the preparation of microcapsules is known, which contains (a) an epoxypropyltrialkylammonium salt and, in addition, an alkyl sulfosuccinate having alkyl groups with 6 to 16 carbon atoms or an alkyl sulfosuccinamate whose carboxylic acid amide group is substituted with an alkyl group with 8 to 20 carbon atoms, and a water-miscible solvent as component (b).

The subject of EP 2 669 835 A1 (KOEHLER) is a process for the production of microcapsules. The characteristic of these microcapsules is a specific particle size distribution having at least two maxima, wherein the main maximum particle size is in the range of 5 to 100 µm and wherein the volume occupied by the microcapsules whose particle size is less than or equal to one quarter of the particle size of the main maximum is greater than or equal to about 20% of the total volume of the microcapsules. In this regard, the capsule wall may consist of a methylated melamine-formaldehyde resin and/or urea-formaldehyde resin and/or reaction products of aldehydes with thiourea, N-alkylurea, guanidine, acetoguanamine, benzoguanamine, caprionoguanamine, cyanamide, dicyandiamide and/or alkyl/arylsulfonamide.

EP 3 238 816 A1 (SYMRISE) discloses a process for the preparation of microcapsules, in particular aminoplast microcapsules, in which the emulsification of the aqueous pre-polymer phase and the non-aqueous phase containing the active ingredient to be encapsulated is carried out in the presence of at least one 1,2-diol, resulting in a significant reduction in the microcapsule particle size and thus in a stabilization of the emulsion.

WO 2017/148504 (SYMRISE) relates to a process for the preparation of fragrance capsules in which a fragrance composition having an acid value of at most 5 mg KOH/g immediately prior to encapsulation is encapsulated with natural coating materials or synthetic, anionic or cationic polymers or mixtures thereof.

Microcapsules can furthermore be made from acrylate monomers, polyureas or even biopolymers such as gelatin and other proteins or inorganic wall materials. In prior art isocyanate-based microcapsules, polyisocyanates are reacted with guanidinium carbonate as crosslinker in an alkaline environment.

The advantage of encapsulation with isocyanates compared to aminoplast resins is that the microcapsules are formaldehyde-free. However, the disadvantage of encapsulation with isocyanates and other wall materials is that only a limited number of active ingredients, for example fragrances or fragrance oils, can be encapsulated with them and provide stable microcapsules. In particular, encapsulation with isocyanates and other wall materials is not suitable for encapsulating fragrances or fragrance oils with aldehyde, carboxylic acid or ester functionalities. This is because during encapsulation at an alkaline pH, carboxylic acids are deprotonated, oxidized aldehydes (carboxylic acids) are analogously saponified and esters are saponified, making the resulting emulsion unstable. Thus, the use of such microencapsulation is limited with regard to the active ingredients and thus suitable, for example, only for a small spectrum of fragrances or fragrance oils, while such microencapsulation is ruled out for fragrances or fragrance oils with aldehyde, carboxylic acid or ester functionalities. However, fragrances with aldehyde, carboxylic acid or ester functionalities are among the most important representatives of fragrances or fragrance oils.

Against this background, the present invention was based on the complex task of providing a process for the production of microcapsules which, on the one hand, allows encapsulation free of formaldehyde fora wide variability with regard to the active ingredients to be encapsulated, in particular active ingredients with aldehyde, carboxylic acid or ester functionalities, and, on the other hand, produces microcapsules which are storage-stable and exhibit excellent release behavior of the active ingredients.

Surprisingly, it was found that this task can be solved by preparing the capsule shell or capsule wall, primarily formed from isocyanates, in an aqueous emulsion in the presence of a protective colloid and a catalyst by two successive crosslinking steps, each with an amine at different pH values. Two-step crosslinking at a pH gradient from acidic to alkaline makes it possible to form a multilayer capsule shell or capsule wall, whereby even active ingredients, such as fragrances, with aldehyde, carboxylic acid or ester functionalities can be encapsulated.

The process engineering advantage is that by crosslinking with a first crosslinker at an acidic pH, the functional groups of the active ingredients to be encapsulated are protected by a first polymer layer before the pH is raised by adding a further, alkaline crosslinker.

SUMMARY OF THE INVENTION

Thus, a first object of the invention relates to a process for the preparation of isocyanate-based microcapsules comprising or consisting of the following steps:
  (a) Providing an internal non-aqueous phase comprising at least one isocyanate having two or more isocyanate groups or at least one isothiocyanate having two or more isothiocyanate groups and a hydrophobic active ingredient to be encapsulated;
  (b) Providing an external aqueous phase comprising at least one protective colloid and a catalyst;
  (c) Mixing the internal non-aqueous phase and the external aqueous phase, optionally in the presence of a stabilizer and/or emulsifier, to obtain an oil-in-water emulsion;
  (d) initial crosslinking by adding an amine that reacts at an acidic pH;
  (e) further crosslinking by addition of an amine reacting at an alkaline pH to obtain microcapsules;
  (f) curing the microcapsules obtained in step (e); and optional (g) Separating the microcapsules from the reaction solution and drying the microcapsules if necessary.

In addition, it is an object of the present invention to provide microcapsules produced by the process according to the invention.

Another aspect of the present invention is microcapsules comprising or consisting of:
- a core comprising or consisting of at least one hydrophobic agent; and
- a capsule shell comprising an isocyanate having at least two or more isocyanate groups which is crosslinked in the presence of a protective colloid and a catalyst in a first step by an amine reacting at an acidic pH and in a further step by an amine reacting at an alkaline pH.

Finally, in another aspect, the present invention relates to the use of the microcapsules according to the invention or suspensions comprising the microcapsules according to the invention for the manufacture of detergents, fabric softeners, detergents, scent boosters (fragrance enhancers), cosmetics, personal care products, agricultural products or pharmaceutical products.

These and other aspects, features and advantages of the present invention will be apparent to those skilled in the art from a study of the following detailed description and claims. In this regard, any feature from one aspect of the invention may be used or substituted in another aspect of the invention. Further, it is understood that the examples contained herein describe and illustrate the invention but are not intended to limit the invention and, in particular, that the present invention is not limited to these examples.

All percentages are by weight unless otherwise stated. Numerical examples given in the form "from x to y" include the values given. When multiple preferred numeric ranges are given in this format, it is understood that all ranges created by combining the various endpoints are also included.

FIGURES

FIG. 6 is a diagram showing the results of a sensory evaluation of prior art microcapsules and microcapsules according to the invention.

DETAILED DESCRIPTION OF THE INVENTION

Figure 1:
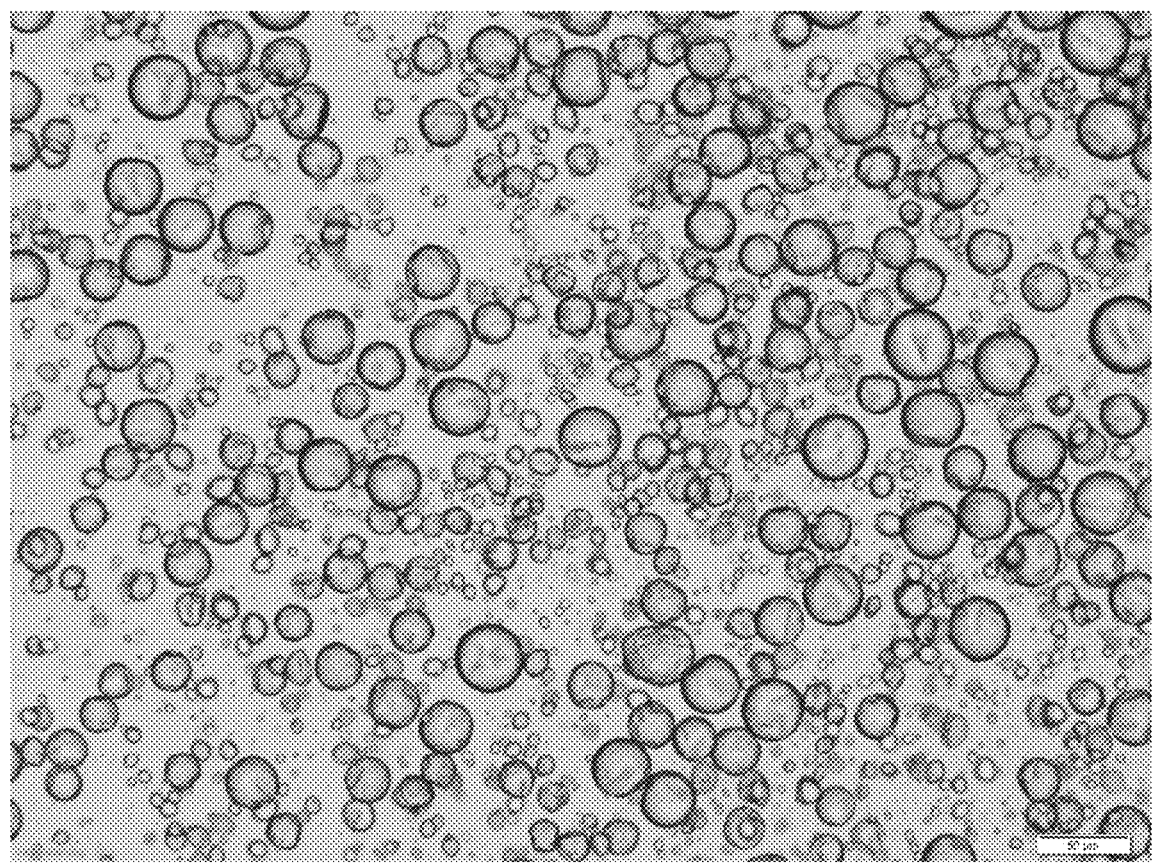
FIG. 1 is a light microscope image of the microcapsules according to the invention at 10× magnification. An Olympus BX51 was used for the light microscopic image.

In a first aspect, the present invention relates to a process for preparing isocyanate-based microcapsules comprising or consisting of the following steps:
(a) Providing an internal non-aqueous phase comprising at least one isocyanate having two or more isocyanate groups or at least one isothiocyanate having two or more isothiocyanate groups and a hydrophobic active ingredient to be encapsulated;
(b) Providing an external aqueous phase comprising at least one protective colloid and a catalyst;
(c) Mixing the internal non-aqueous phase and the external aqueous phase, optionally in the presence of a stabilizer and/or emulsifier, to obtain an oil-in-water emulsion;
(d) initial crosslinking by adding an amine that reacts at an acidic pH;
(e) further crosslinking by addition of an amine reacting at an alkaline pH to obtain microcapsules;
(f) curing the microcapsules obtained in step (e); and optional
(g) Separating the microcapsules from the reaction solution and drying the microcapsules if necessary.

In the context of the present invention, microcapsules are understood to be microparticles that have a capsule shell or capsule wall and one or more hydrophobic active ingredient(s) as the core material inside the capsule.

In a first step of the process according to the invention, an internal non-aqueous phase is provided comprising at least one isocyanate having at least two or more isocyanate groups and a hydrophobic active ingredient to be encapsulated.

The isocyanate compounds or isocyanate monomers which can be polymerized according to the invention to form the capsule shell or capsule wall are isocyanates or isothiocyanates having at least two, three, four or more highly functional isocyanate groups or isothiocyanate groups, in particular aliphatic, cycloaliphatic, hydroaromatic, aromatic or heterocyclic polyisocyanates or polyisothiocyanates, their substitution products and mixtures of the above compounds. Among the polyisocyanates, diisocyanates are preferred. Even more preferred are aromatic diisocyanates.

By using mixtures of at least two different polymerizable compounds containing isocyanate or isothiocyanate groups, copolymers can also be prepared.

Examples of monomers containing at least two isocyanate groups or at least two isothiocyanate groups which can be used according to the invention are: ethylene diisocyanate, trimethylene diisocyanate, 1,4-tetramethylene diisocyanate, 1,6-hexamethyldiisocyanate, ethylene diisothiocyanate, tetramethylene diisothiocyanate, hexamethylene diisothiocyanate, cyclobutane-1,3-diisocyanate, cyclohexane-1,3-diisocyanate, cyclohexane-1,4-diisocyanate, 1,3-phenylene diisocyanate, 1,4-phenylene diisocyanate, mixtures of 1,3-phenylene diisocyanate and 1,4-phenylene diisocyanate, p-phenylene diisothiocyanate, xylylene-1,4-diisothiocyanate, 2,4-toluylene diisocyanate, 2,6-toluylene diisocyanate, mixtures of 2,4-toluylene diisocyanate and 2,6-toluylene diisocyanate, xylylene-1,4-diisocyanate, xylylene-1,3-diisocyanate and mixtures of xylylene-1,4-diisocyanate and xylylene-1,3-diisocyanate, 2,4-hexahydrotoluylene diisocyanate, 2,6-hexahydrotoluylene diisocyanate, mixtures of 2,4-hexahydrotoluylene diisocyanate and 2,6-hexahydrotoluylene diisocyanate, hexahydro-1,3-phenylene diisocyanate, hexahydro-1,4-phenylene diisocyanate, mixtures of hexahydro-1,4-phenylene diisocyanate and hexahydro-1,4-phenylene diisocyanate, 1,3-diisocyanatobenzene, 1,3,5-trimethyl benzene-2,4-diisocyanate, 1,3,5-triisopropylbenzene-2,4-diisocyanate, diphenylmethane-4,4'-diisocyanate, 3,3'-dimethyldiphenylmethane-4,4'-diisocyanate, 4,4'-diphenylpropane diisocyanate, naphthylene-1,4-diisocyanate, naphthylene-1,5-diisocyanate, triphenylmethane-4,4',4"-triisocyanate, toluene-2,4,6-triisocyanate, dimethyldiphenylmethane-2,2',5,5'-tetraisocyanate or mixtures of the above compounds.

Preferred polymerizable compounds containing at least two isocyanate or isothiocyanate groups are industrially produced di- and polyisocyanates, for example TDI: toluylene diisocyanate (isomer mixture of 2,4- and 2,6-toluylene diisocyanate in a ratio of 80:20), HDI: hexamethylene diisocyanate-(1,6), IPDI: isophorone diisocyanate or DMDI: diphenylmethane-4,4'-diisocyanate.

Other starting isocyanates used in the process according to the invention are: Diisocyanates such as 1,4-diisocyanatobutane, 1,6-diisocyanatohexane, 1,5-diisocyanato-2,2-dimethylpentane, 2,2,4- and 2,4,4-trimethyl-1,6-diisocyanatohexane, 1,10-diisocyanatodecane, 1,3- and 1,4-diisocyanatocyclohexane, 1-isocyanato-3,3,5-trimethyl-5-isocyanatomethylcyclohexane (isophorone diisocyanate), 4,4'-diisocyanatodicyclohexylmethane, 2,4- and 2,6-diisocyanato-methylcyclohexane and mixtures thereof. In principle, aromatic isocyanates, e.g. toluylene diisocyanates or 4,4'-diisocyanato-diphenylmethane, can also be used.

Polyisocyanates which can be prepared by modifying the above-mentioned diisocyanates or mixtures thereof by known methods and which contain, for example, uretdione, urethane, isocyanurate, biuret and/or allophanate groups can also be used proportionally.

The proportion of the isocyanate component in the internal non-aqueous phase is in a range from 1 to 8 wt %, preferably in a range from 3 to 7 wt %, based on the total weight of the non-aqueous phase. Most preferably, the isocyanate component in the internal non-aqueous phase is in a range of 5 to 6 wt %, based on the total weight of the non-aqueous phase.

Any material suitable for inclusion in microcapsules can be used as a core material for the production of microcapsules according to the invention. Preferably, hydrophobic, water-insoluble or water-immiscible liquids or solids as well as suspensions can be considered as materials to be encapsulated. In the context of the present description, the term "hydrophobic material" means that the material to be encapsulated is in the internal non-aqueous phase and does not mix with the external aqueous phase.

In a particularly preferred embodiment, the microcapsules according to the invention are designed in such a way that they comprise a core material of at least one hydrophobic active ingredient, in particular a hydrophobic fragrance or a hydrophobic fragrance oil, a pesticide, a biocide, an insecticide, a substance from the group of repellents, food additives, cosmetic active ingredients, pharmaceutical active ingredients, dyes, agrochemicals, dyes, luminous dyes, optical brighteners, solvents, waxes, silicone oils, lubricants, as well as mixtures of the aforementioned active ingredients, i.e., as long as it is sufficiently water-repellent, the microcapsules according to the invention have a core material of at least one hydrophobic active ingredient, in particular a hydrophobic fragrance or a hydrophobic fragrance oil i.e. as long as it is sufficiently insoluble in water or does not mix with the water phase, otherwise no emulsion can form and no deposition of the polymer on the droplet surface can take place.

In a preferred embodiment of the first aspect of the present invention, the active ingredients may be, in particular, hydrophobic fragrances or fragrance oils, flavors or biogenic principles.

In a preferred embodiment, the microcapsules according to the invention have a core material in the form of a hydrophobic single fragrance or single odorant, wherein the core material comprises at least one single fragrance or single odorant, or mixtures thereof, selected from one or more of the following groups:

hydrocarbons, such as 3-carene; a-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene;

Aliphatic alcohols, such as hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3,4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

Aliphatic aldehydes and their acetals, such as hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanaldiethyl acetal; 1,1-dimethoxy-2,2,5-trimethyl-4-hexene; citronellyloxyacetaldehyde;

Aliphatic ketones and their oximes, such as 2-heptanone; 2-octanone; 3-octanone; 2-nonanone; 5-methyl-3-heptanone; 5-methyl-3-heptanone oxime; 2,4,4,7-tetramethyl-6-octen-3-one;

Aliphatic sulfur-containing compounds, such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

Aliphatic nitriles, such as 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

Aliphatic carboxylic acids and their esters, such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; Methyl 3,7-dimethyl 2,6-octadienoate;

Acyclic terpene alcohols, such as citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerianates, pentanoates, hexanoates, crotonates, tiglinates, 3-methyl-2-butenoates;

Acyclic terpene aldehydes and ketones, such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethylacetals of geranial, neral, 7-hydroxy-3,7-dimethyloctanal;

Cyclic terpene alcohols, such as menthol; isopulegol; a-terpineol; terpinenol-4; menthan-8-ol; menthan-1-ol;

menthan-7-ol; borneol; isoborneol; linalool oxide; nopol; cedrol; ambrinol; vetiverol; guajol; and their formates, acetates, propionates, isobutyrates, butyrates, isovalerianates, pentanoates, hexanoates, crotonates, tiglinates, 3-methyl-2-butenoates;

Cyclic terpene aldehydes and ketones, such as Menthane; isomenthone; 8-mercaptomenthan-3-one; carvone; camphor; fenchone; α-ionone; beta-ionone; α-n-methylionone; beta-n-methylionone; α-isomethylionone; beta-isomethylionone; α-irone; ß-irone; α-damascenone; beta-damascenone; gamma-damascenone; d-damascenone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; α-sinene sal; beta-sinene sal; acetylated cedarwood oil (methylcedryl ketone);

Cyclic alcohols, such as 4-tert-butylcyclohexanol; 3,3,5-trimethylcyclohexanol; 3-isocamphylcyclohexanol; 2,6,9-trimethyl-(Z2,Z5,E9)-cyclododecatrien-1-ol; 2-isobutyl-4-methyltetrahydro-2H-pyran-4-ol; from the group of cycloaliphatic alcohols such as 3,3,3-trimethyl-cyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers, such as cineol; cedryl methyl ether; cyclododecyl methyl ether; (ethoxymethoxy)cyclododecane; a-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

Cyclic ketones, such as 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

Cycloaliphatic aldehydes, such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones, such as 1-(3,3-dimethylcyclohexyl)-4-penten-1-one; 1-(5,5-dimethyl-2-cyclohexen-1-yl)-4-penten-1-one; 2,3,8,8-tetramethyl-1,2,3,4,5,6,7,8-octahydro-2-naphthalenyl methyl ketone; Methyl-2,6,10-trimethyl-2,5,9-cyclododecatrienyl ketone; tert-butyl-(2,4-dimethyl-3-cyclohexen-1-yl)ketone;

Esters of cyclic alcohols, such as 2-tert-butyl cyclohexyl acetate; 4-tert-butyl cyclohexyl acetate; 2-tert-pentyl cyclohexyl acetate; 4-tert-pentyl cyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate;

Esters of cycloaliphatic carboxylic acids, such as allyl 3-cyclohexyl propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic hydrocarbons, such as styrene and diphenylmethane;

Araliphatic alcohols, such as benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenyl-ethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids, such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; α-trichloromethyl benzyl acetate; a,a-dimethylphenylethyl acetate; a,a-dimethylphenylethyl butyrate; cinnamyl acetate; 2-phenoxyethyl isobutyrate; 4-methoxybenzyl acetate;

Araliphatic ethers, such as 2-phenylethyl methyl ether; 2-phenylethyl isoamyl ether; 2-phenylethyl-1-ethoxyethyl ether; phenylacetaldehyde dimethylacetal; phenylacetaldehyde diethylacetal; hydratropaaldehyde dimethylacetal; Phenylacetaldehyde glycerol acetal; 2,4,6-trimethyl-4-phenyl-1,3-dioxanes; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes, such as benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; a-butylcinnamaldehyde; a-amylcinnamaldehyde; a-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

Aromatic and araliphatic ketones, such as acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]

ethanone; 5',6',7',8'-tetrahydro-3',5',5',6',8',8'-hexamethyl-2-acetonaphthone;

Aromatic and araliphatic carboxylic acids and their esters, such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenyl glycidate; ethyl 3-methyl-3-phenyl glycidate;

Nitrogen-containing aromatic compounds, such as 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl N-methyl anthranilate; Schiff bases of methylanthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; scatole; 2-methoxy-3-isopropylpyrazine; 2-isobutyl-3-methoxypyrazine; 4-(4,8-dimethyl-3,7-nonadienyl)-pyridine;

Phenols, phenyl ethers and phenyl esters, such as tarragol; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate; from the group of heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

Lactones, such as. 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 1,15-pentadecanolide; cis- and trans-11-pentadecene-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin;

as well as the stereoisomers, enantiomers, positional isomers, diastereomers, cis/trans isomers and epimers, respectively, of the substances mentioned above.

In an alternative embodiment, fragrance oils or perfume oils are used as the core material. These are compositions containing at least one fragrance material. Such compositions, in particular fragrance oils or perfume oils, preferably comprise two, three, four, five, six, seven, eight, nine, ten or more oderous substances. The fragrance oils or perfume oils are preferably selected from the group of extracts from natural raw materials, such as essential oils, concretes, absolutes, resins, resinoids, balsams, tinctures such as. Ambergris oil; Amyris oil; *Angelica* seed oil; *Angelica* root oil; Anise oil; Valerian oil; Basil oil; Tree moss absolu; Bay oil; Mugwort oil; Benzöresin; Bergamot oil; Beeswax absolu; Birch tar oil; Bitter almond oil; Savory oil; Bucco leaf oil; Cabreuva oil; Cade oil; Calmus oil; Camphor oil; *Cananga* oil; Cardamom oil; Cascarilla oil; *Cassia* oil; Cassie absolu; Castoreum absolu; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolu; Oak moss absolu; Elemi oil; Tarragon oil; *Eucalyptus citriodora* oil; *Eucalyptus* oil; Fennel oil; Spruce needle oil; *Galbanum* oil; *Galbanum* resin; Geranium oil; Grapefruit oil; Guaiac wood oil; Gurjun balsam; Gurjun balsam oil, Helichrysum absolu; Helichrysum oil; Ginger oil; Iris root absolute; Iris root oil; Jasmine absolute; Calamus oil; Chamomile oil blue; Chamomile oil Roman; Carrot seed oil; Cascarilla oil; Pine needle oil; Curly mint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linal oil; *Litsea cubeba* oil; Bay leaf oil; Macis oil; Marjoram oil; Mandarin oil; Masso bark oil; *Mimosa* absolu; Musk grain oil; Musk tincture; Muscat oil; Myrrh absolu; Myrrh oil; Myrtle oil; Clove leaf oil; Clove flower oil; Neroli oil; Olibanum absolu; Olibanum oil; *Opopanax* oil; Orange flower absolu; Orange oil; *Origanum* oil; Palmarosa oil; Patchouli oil; *Perilla* oil; Perubalsam oil; Parsley leaf oil; Parsley seed oil; Petitgrain oil; Peppermint oil; Pepper oil; Allspice oil; Pine oil; Poley oil; Rose absolu; Rosewood oil; Rose oil; Rosemary oil; Sage oil Dalmatian; Sage oil Spanish; Sandalwood oil; Celery seed oil; Spicy lavender oil; Star anise oil; *Styrax* oil; *Tagetes* oil; Fir needle oil; Tea tree oil; Turpentine oil; thyme oil; tolu balsam; tonka absolute; tuberose absolute; vanilla extract; violet leaf absolute; *verbena* oil; vetiver oil; juniper berry oil; wine yeast oil; wormwood oil; wintergreen oil; ylang oil; hyssop oil; civet absolute; cinnamon leaf oil; cinnamon bark oil; and fractions thereof or ingredients isolated therefrom.

Of the above-mentioned individual fragrances or individual odorants which can be encapsulated in the sense of the present invention, fragrances or odorants which have an aldehyde, carboxylic acid or ester functionality are particularly preferred for use.

Aldehydic fragrances or odorants, which also include the corresponding acetals as well as esters and lactones, can be divided into the following groups, namely.

(i) aliphatic aldehydes and their acetals;
(ii) cycloaliphatic aldehydes;
(iii) aromatic or araliphatic aldehydes;
(iv) aliphatic, aromatic or araliphatic esters; and
(v) Lactones;
and mixtures thereof.

The aforementioned fragrances or odorants with aldehyde, carboxylic acid or ester functionality, as well as mixtures thereof, are selected from one or more of the following groups:

Aliphatic aldehydes and their acetals, such as hexanal; heptanal; octanal; nonanal; decanal; undecanal; dodecanal; tridecanal; 2-methyloctanal; 2-methylnonanal; (f)-2-hexenal; (Z)-4-heptenal; 2,6-dimethyl-5-heptenal; 10-undecenal; (f)-4-decenal; 2-dodecenal; 2,6,10-trimethyl-5,9-undecadienal; heptanal diethylacetal; 1,1-dimethoxy-2,2,5-trimethyl-4-hexene; citronellyloxyacetaldehyde;

Cycloaliphatic aldehydes, such as 2,4-dimethyl-3-cyclohexenecarbaldehyde; 2-methyl-4-(2,2,6-trimethyl-cyclohexen-I-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Aromatic and araliphatic aldehydes, such as benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; α-butylcinnamaldehyde; α-amylcinnamaldehyde; α-hexylcinnamaldehyde; 3-methyl-5-phenylpentanal; 4-methoxybenzaldehyde; 4-hydroxy-3-methoxybenzaldehyde; 4-hydroxy-3ethoxybenzaldehyde; 3,4-methylenedioxybenzaldehyde; 3,4-dimethoxybenzaldehyde; 2-methyl 3-(4-methoxyphenyl)propanal; 2-methyl 3-(4-methylenedioxyphenyl)propanal;

Aliphatic carboxylic acid esters, such as. (E)- and (Z)-3-hexenyl formate; ethyl acetoacetate; isoamyl acetate; hexyl acetate; 3,5,5-trimethylhexyl acetate; 3-methyl-2-butenyl acetate; (f)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; Ethyl octanoate; Ethyl (E,Z)-2,4-decadienoate; Methyl 2-octinate; Methyl 2-noninate; Allyl 2-isoamyloxyacetate; Methyl 3,7-dimethyl 2,6-octadienoate;

Esters of cyclic alcohols, such as. 2-tert-butyl cyclohexyl acetate; 4-tert-butyl cyclohexyl acetate; 2-ieri-pentyl cyclohexyl acetate; 4-tert-pentyl cyclohexyl acetate; decahydro-2-naphthyl acetate; 3-pentyl tetrahydro-2/-/-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate;

Esters of araliphatic alcohols and aliphatic carboxylic acids, such as. Benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; a-trichloromethyl benzyl acetate; α,α-dimethylphenylethyl acetate; α,α-dimethylphenylethyl butyrate; cinnamyl acetate; 2-phenoxyethyl isobutyrate; 4-methoxybenzyl acetate;

Esters of cycloaliphatic carboxylic acids, such as allyl 3-cyclohexyl propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic and araliphatic carboxylic acid esters, such as methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenyl glycidate; ethyl 3-methyl-3-phenyl glycidate.

Listed below are aldehydes, acetals, esters and lactones with their commercial designations which are particularly preferred as representatives of groups (i) to (v) for the purposes of the process according to the invention:

Aldehydes: 2-methylpentanal; aldehyde c12 mna hm; aldehydes c 4; aldehydes c 5; aldehydes c 6; aldehydes c 7; aldehydes c 8; aldehydes c 9; aldehydes c 10; aldehydes c 11 iso; aldehydes c 11 moa pure; aldehydes c 11 undecanal; aldehydes c 11 undeylenic; aldehydes c 12; aldehydes c 12 mna; aldehydes c 13; aldehyde madarine; amyl cinnamic aldehyde alpha; anisalaldehyde-o; anisyl aldehyde; benzaldehyde nat.; bergamal; boronal; bourgeonal; camphonelic aldehyde; citral; citronellal hm; citronellyl oxyacet aldehyde; citrylal; citroylal e hm; cortex aldehyde; cortex aldehyde 50 pct pemosa; crotonic aldehyde; cuminal aldehyde; cyclamen aldehyde; decadienal trans, trans-2,4, decanal cis-4; decanal trans-2; decanal trans-2 nat; decanal trans-4; decanal-9,1; dodecanienal 2,6; dodecanal trans-2; dupical; epoxydecenal-4,5-2 10% tri; ethyl hexanal; Farenal®; florhydral; geraldehyde; helional; heliopan; heliotropin; heptadienal trans, trans,2-4; heptenal cis-4; heptenal trans-2; hexenal trans-2; hexyl cinnamic aldehyde alpha; hydratropic aldehyde; hydroxy citronellal; intreleven aldehyde spec.; isononyl aldehyde; isovaleric aldehyde; lemon aldehyde h&r js i; lilial; linolal; lyral; majantal; mandrinal; mandraine aldehyde 10% in tec bht; mefranal; Melonal®; methody citronellal; methyl butyraldehyde; methyl cinnamic aldehyde alpha; methyl phenylpentenal-4,2,2; methyl thio propanal-3; methyl tridecanal-12 10% vt; methyl-3-buten-2-al; methyl-5-phenyl-2-hexene-2-al; mugenal 50 dpg; neocyclo citral; nonadienal; trans, cis-2,6; nonenal cis-6; nonenal trans-2; Oncidal® 3/060251; pentenal trans-2; *perilla* aldehyde; phenylacet aldehyde; phenylbutenal trans-2,2; phenylpropyl aldehyde; pinoacet aldehyde; profranesal; propionalaldehyde 2-(p-tolyl); propionic aldehyde; ps-iraldein x neu; safranal; salicylic aldehyde fg; silvial; tetrahydro citral; tiglic aldehyde-2,2; tolyl aldehyde para fg; tridecenal trans-2; trifernal; undecadienal-2,4; undecenal trans-2; vernalaldehyde; vertocitral; vertomugal; vertiprenal; vetral crude; cinnamaldehyde nat. hm; acetals: floropal; heptanal diethyl acetal; nonandienal diethyl acetal; okoumal; phenylacet ald. glycerin acetal; phenylacetaldeyhdedimethylacetal; ester: jasmal; jessemal; kharismal; Tiramisone®.

In a further variant of the process according to the invention, flavoring substances can also be encapsulated as a core material in the form of a single flavoring substance, the core material comprising at least one single flavoring substance or mixtures thereof.

Typical examples of flavors that may be encapsulated in accordance with the invention are selected from the group consisting of: Acetophenone; allyl capronate; alpha-ionone; beta-ionone; anisaldehyde; anisyl acetate; anisyl formate; benzaldehyde; benzothiazole; benzyl acetate; benzyl alcohol; benzyl benzoate; beta-ionone; butyl butyrate; butyl capronate; butylidene phthalide; carvone; camphene; caryophyllene; cineole; cinnamyl acetate; citral; citronellol; citronellal; citronellyl acetate; cyclohexyl acetate; cymene; damascone; decalactone; dihydrocoumarin; dimethylanthranilate; dimethyl anthranilate; dodecalactone; ethoxyethyl acetate; ethyl butyric acid; ethyl butyrate; ethyl caprinate; ethyl capronate; ethyl crotonate; ethyl furaneol; ethyl guaiacol; ethyl isobutyrate; ethyl isovalerate; ethyl lactate; ethyl methyl butyrate; ethyl propionate; eucalyptol; eugenol; ethyl heptylate; 4-(p-hydroxyphenyl)-2-butanone; gamma-decalactone; geraniol; geranyl acetate; geranyl acetate; grapefruit aldehyde; methyl dihydro jasmonate (e.g. Hedion®); heliotropin; 2-heptanone; 3-heptanone; 4-heptanone; trans-2-heptenal; cis-4-heptenal; trans-2-hexenal; cis-3-hexenol; trans-2-hexenoic acid; trans-3-hexenoic acid; cis-2-hexenyl acetate; cis-3-hexenyl acetate; cis-3-hexenyl capronate; trans-2-hexenyl capronate; cis-3-hexenyl formate; cis-2-hexyl acetate; cis-3-hexyl acetate; trans-2-hexyl acetate; cis-3-hexyl formate; para-hydroxybenzylacetone; isoamyl alcohol; isoamyl isovalerate; isobutyl butyrate; isobutyraldehyde; isoeugenol methyl ether; isopropyl methyl thiazole; lauric acid; leavulinic acid; linalool; linalool oxide; linalyl acetate; menthol; menthofuran; methyl anthranilate; methyl butanol; methyl butyric acid; 2-methyl butyl acetate; methyl capronate; methyl cinnamate; 5-methyl furfural; 3,2,2-methylcyclopentenolone; 6,5,2-methylheptenone; methyl dihydrojasmonate; methyl jasmonate; 2-methyl methyl butyrate; 2-methyl 2-pentenolic acid; methyl thiobutyrate; 3,1-methylthiohexanol; 3-methylthiohexyl acetate; nerol; neryl acetate; trans,trans-2,4-nonadienal; 2,4-nonadienol; 2,6-nonadienol; 2,4-nonadienol; nootkatone; delta-octalactone; gamma-octalactone; 2-octanol; 3-octanol; 1,3-octenol; 1-octyl acetate; 3-octyl acetate; palmitic acid; Paraldehyde; phellandrene; pentanedione; phenylethyl acetate; phenylethyl alcohol; phenylethyl alcohol; phenylethyl isovalerate; piperonal; propionaldehyde; propyl butyrate; pulegone; pulegol; sinensal; sulfurol; terpinene; terpineol; terpinolene; 8,3-thiomenthanone; 4,4,2-thiomethylpentanone; thymol; delta-undecalactone; gamma-undecalactone; valencene; valeric acid; vanillin; acetoin; ethylvanillin; ethylvanillin isobutyrate (3-ethoxy-4-isobutyryloxybenzaldehyde); 2,5-dimethyl-4-hydroxy-3(2H)-furanone and its derivatives (preferably homofuraneol (2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone); maltol and maltol derivatives (preferably ethylmaltol); coumarin and coumarin derivatives; gamma-lactones (preferably gamma-undecalactone, gamma-nonalactone, gamma-decalactone); delta-lactones (preferably 4-methyldeltadecalactone, massoilactone, deltadecalactone, tuberolactone); methyl sorbate; divanillin; 4-hydroxy-2(or 5)-ethyl-5(or 2)-methyl-3(2H)furanone; 2-hydroxy-3-methyl-2-cyclopentenone; 3-hydroxy-4,5-dimethyl-2(5H)-furanone; Acetic acid isoamyl ester; Butyric acid ethyl ester; Butyric acid n-butyl ester; Butyric acid isoamyl ester; 3-Methyl butyric acid ethyl ester; n-Hexanoic acid ethyl ester; n-Hexanoic acid allyl ester; n-Hexanoic acid n-butyl ester; n-Octanoic acid ethyl ester; Ethyl 3-methyl-3-phenyl glycidate; ethyl 2-trans-4-cis-decadienoate; 4-(p-hydroxyphenyl)-2-butanone; 1,1-dimethoxy-2,2,5-trimethyl-4-hexane; 2,6-dimethyl-5-heptene-1-al; phenylacetaldehyde; 2-methyl-3-(methylthio)furan; 2-methyl-3-furanthiol; bis(2-methyl-3-furyl)disulfide; furfuryl mercaptan; methional; 2-acetyl-2-thiazoline; 3-mercapto-2-pentanone; 2,5-dimethyl-3-furanthiol; 2,4,5-trimethylthiazole; 2-acetylthiazole; 2,4-dimethyl-5-ethylthiazole; 2-acetyl-1-pyrroline; 2-methyl-3-ethylpyrazine; 2-ethyl-3,5-dimethylpyrazine; 2-ethyl-3,6-dimethylpyrazine; 2,3-diethyl-5-methylpyrazine; 3-isopropyl-2-methoxypyrazine; 3-isobutyl-2-methoxypyrazine; 2-acetylpyrazine; 2-pentylpyridine; (E,E)-2,4-decadienal; (E,E)-2,4-nonadienal; (E)-2-octenal; (E)-2-nonenal; 2-undecenal; 12-methyltridecanal; 1-penten-3-one; 4-hydroxy-2,5-dimethyl-3(2H)-furanone; guaiacol; 3-hydroxy-4,5-dimethyl-2(5H)-furanone; 3-hydroxy-4-methyl-5-ethyl-2(5H)-furanone; cinnamaldehyde; cinnamalcohol; methyl salicylate; isopulegol and the stereoisomers, enantiomers, positional isomers, diastereomers, cis/trans isomers and epimers, respectively, of these substances not explicitly mentioned herein. epimers of these substances.

Most preferably, perfumes or fragrances or flavoring agents are used in the preparation of the isocyanate-based microcapsules, which are selected from the group consisting of: agrumex Ic; agrunitrile; aldehyde c11 undecylenic; aldehyde c12 lauric; aldehyde c12 mna; aldehyde c14 sog; aldehyde c16 sog.; allylamylglycolate; allylcapronate; allylcyclohexylpropionate; allylheptylate; Ambrocenide® 10 tec; Ambrocenide® krist. 10% ipm; ambroxide; anethol nat. ex sternanis; anisaldehyde pure; Aprifloren®; benzyl acetone; benzyl salicylate; borneol 1/isoborneol 65/35; buccoblaetteroel; citronellol 950; clonal; cyclohexyl salicylate; cymol para supra; damascone delta; dihydromyrcenol; dimethylbenzylcarbinyl butyrate; dynascone; ethylene brassylate; ethyl methyl butyrate-2; ethyl saffronate; eucalyptol nat.; *eucalyptus* oil globulus 80/85%; eugenol nat.; Farenal®; fennel oil aroma type sweet nat.; filbertone 10% ipm; filbertone; floropal; galbascone; geraniol 60; Globanone®; hedione; herbaflorate; herbanate; herbyl propionate; hexenyl acetate cis-3; hexenyl salicylate cis-3; hexylacetate; hexylacetate s; hexyl isobutyrate; hexyl salicylate; isoamyl butyrate; isobornyl acetate; isopropyl methyl butyrate-2; isoraldein 70; javanol; camphor dl; cresol methyl ether p(cr<10 ppm); lemonile; ligustral; lilial; linalool; manzanate; melonal; methylheptin carbonate; methyloctin carbonate; muscenone; neocycloctiral; nerolin bromelia; nerolin yara yara cryst.; nerolione; norlimbanol; orangenoel; orivone; ozonil; patchoulioel entf.; vegetable oil triglyceride; phellandrene fraction ex *eucalyptus* oil; Pheniraf®; phenylethyl acetate; rose oxide high cis; Sandranol®; styrene acetate; Sultanene®; terpinen gamma; tetrahydrolinalool; timbersilk; triethylcitrate; undecavertol; vertocitral; vertofix; Ysamber® k and mixtures of the above active ingredients.

In a further variant of the process according to the invention, biogenic principles can also be encapsulated as core material, wherein the core material comprises at least one biogenic principle or mixtures thereof.

Biogenic principles are active ingredients with biological activity, for example tocopherol, tocopherol acetate, tocopherol palmitate, ascorbic acid, carnotine, carnosine, caffeine, (deoxy)ribonucleic acid and its fragmentation products, β-glucans, retinol, bisabolol, allantoin, phytantriol, panthenol, AHA acids, amino acids, ceramides, pseudoceramides, essential oils, plant extracts, and vitamin complexes.

In the process for preparing the isocyanate-based microcapsules according to the invention, the first step is to dissolve the monomer containing at least two isocyanate or isothiocyanate groups described above in an inert solvent or solvent mixture together with the hydrophobic active ingredient to be encapsulated. The organic hydrophobic oily phase thus formed forms the internal non-aqueous phase.

Inert solvents for the internal non-aqueous phase include: chlorinated diphenyl, chlorinated paraffin, vegetable oils such as cottonseed oil, peanut oil, palm oil, tricresyl phosphate, silicone oil, dialkyl phthalates, dialkyl adipates, partially hydrogenated terphenyl, alkylated biphenyl, alkylated naphthalene, diaryl ether, aryl alkyl ether and higher alkylated benzene, benzyl benzoate, isopropyl myristate, and any mixtures of these hydrophobic solvents and mixtures of single or multiple of these hydrophobic solvents with kerosene, paraffines and/or isoparaffins. Preferably, vegetable oil triglycerides, benzyl benzoate or isopropyl myristate are used as solvents for providing the internal non-aqueous phase.

The internal non-aqueous phase may contain, for example, 20 to 50 wt %, preferably 25 to 45 wt % and even more preferably 33 to 40 wt % of hydrophobic active ingredient to be encapsulated, 1 to 8 wt %, preferably 3 to 7 wt % and even more preferably 5 to 6 wt % of isocyanate, complementarily hydrophobic solvents to 100 wt %, based on the total weight of the internal non-aqueous phase.

The internal non-aqueous phase, which comprises at least one isocyanate having two or more isocyanate groups and at least one hydrophobic active ingredient, is emulsified in an external aqueous or hydrophilic phase to form an oil-in-water emulsion.

The external aqueous phase comprises at least one protective colloid and at least one catalyst.

A protective colloid is a compound which prevents the primary particles from clumping together (agglomeration, aggregation, flocculation, coagulation) in precipitation reactions, i.e. in reactions in which a solid phase is deposited from a homogeneous liquid phase. The protective colloid attaches itself to the primary particles with its hydrophobic part and turns its polar, i.e. hydrophilic, molecular part towards the aqueous phase. Through this attachment to the interface, it lowers the interfacial tension and prevents agglomeration of the primary particles. It also stabilizes the emulsion and promotes the formation of comparatively smaller droplets and thus also corresponding microcapsules.

The protective colloid used in the process according to the first aspect of the present invention is selected from the group consisting of diols, in particular ethanediol, 1,2-propanediol, 1,3-propanediol, 1,2-butanediol, isomeric butanediol, 1,2-pentanediol, 1,2-hexanediol, 1,2-octanediol, 1,2-decanediol, 1,2-dodecanediol, and polyols, in particular triols, such as glycerol as well as its ethoxylation and propoxylation products, trimethylolpropane and its ethoxylation and propoxylation products, polyvinyl alcohol and its derivatives, such as ammonium- or sulfonate-functionalized polyvinyl alcohols, polyphenols, preferably 1,3,5-trihydroxybenzene, starch, in particular starch from wheat, potatoes, corn, rice, tapioca or oats, or chemically, mechanically and/or enzymatically modified starch, and mixtures of the above compounds.

Other protective colloids that can be added to the external aqueous phase to stabilize the emulsion are preferably carboxymethylcellulose or polyvinylpyrrolidone, which is commercially available under the name Luviskol®, for example, as well as mixtures of the aforementioned compounds.

Most preferably, polyols, polyphenols or starch, in particular modified starch, are used as protective colloid. Polyvinyl alcohol or its ammonium derivatives, 1,3,5-trihydroxybenzene or modified starch are particularly preferred as protective colloid for the production of the microcapsules according to the invention.

The aforementioned compounds have a dual function: on the one hand, they react with the isocyanate(s), forming stable microcapsules, and on the other hand, they act as protective colloids, preventing the agglomeration of the solid particles, stabilizing the emulsion and thus promoting the formation of small droplets.

Surprisingly and particularly advantageously, one of the above-mentioned protective colloids is used in the external aqueous phase in combination with starch or modified starch as a further protective colloid. Such a combination promotes a reaction between the protective colloid and the isocyanate (s).

Most preferred is the combined use of a protective colloid with modified starch. The use of one of the aforementioned combinations has the advantage, on the one hand, that the solid phase in the formulation cannot flocculate and the emulsion is stabilized and, on the other hand, the joint use results in particularly stable microcapsules.

A polyphenol, preferably 1,3,5-trihydroxybenzene, with starch or modified starch has proven to be a particularly advantageous combination. Most preferred is a combination of 1,3,5-trihydroxybenzene with modified starch.

The 1,3,5-trihydroxybenzene is used as a hydroxyl group donor; to provide corresponding groups in protective colloids without hydroxyl groups, thus providing a gain in stability.

The amount of protective colloid used, or the amount of a combination of protective colloids used, ranges from 1 to 8% by weight, preferably from 2 to 4% by weight, even more preferably from 3 to 4% by weight, based on the total weight of the external aqueous phase.

The ratio of protective colloid in the external aqueous phase to isocyanate or isothiocyanate in the internal non-aqueous phase is in a range from 1:5 to 1:100, preferably in a range from 1:10 to 1:75, even more preferably in a range from 1:25 to 1:50.

The catalyst used in the external aqueous phase in the process according to the invention is preferably diazobicyclo[2.2.2]octane (DABCO). DABCO, also known as triethylenediamine (TEDA), is a bicyclic tertiary amine. DABCO is used as a catalyst for the production of polyurethane plastics. The tertiary amine with free electron pairs promotes the reaction between the isocyanate in the internal non-aqueous phase and the protective colloid in the external aqueous phase.

The amount in which the catalyst is added to the external aqueous phase is in a range from 0.001 to 1% by weight, preferably in a range from 0.02 to 0.75% by weight and particularly preferably in a range from 0.05 to 0.5% by weight, based on the total weight of the external aqueous phase. However, the catalyst can also be increased in the case of sluggish polymerization.

Emulsion formation (in the case of liquid active ingredients) or suspension formation (in the case of solid active ingredients), i.e. emulsification or suspension of the internal non-aqueous or oily phase with the external aqueous or hydrophilic phase, takes place under high turbulence or strong shear, the strength of the turbulence or shear determining the diameter of the microcapsules obtained. The production of the microcapsules can be continuous or discontinuous. As the viscosity of the aqueous phase increases or the viscosity of the oily phase decreases, the size of the capsules generally decreases.

Surprisingly, it was found that when the internal non-aqueous phase is emulsified or suspended in the external aqueous phase in the presence of the protective colloid, preferably a polyol, a capsule shell or capsule wall is formed near the core by interfacial polymerization at the interfaces of the emulsified or suspended hydrophobic particles to be encapsulated, which form the core of the microcapsule according to the invention. The formation is based on the polyaddition reaction of the polyisocyanate with the protective colloid, preferably a polyol, to form a capsule shell or capsule wall of polyurethane according to the following formula:

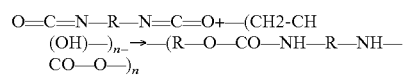

This is shown by gas evolution and release of carbon dioxide.

It can be advantageous if, for the production of the isocyanate-based microcapsules according to the present invention, the external aqueous phase optionally contains further protective colloids and/or stabilizers and/or emulsifying aids either dissolved or dispersed. Such agents can be added, for example, in amounts of from 0.05 to 5% by weight, preferably from 0.1 to 4% by weight, based on the total weight of the aqueous phase.

Preferably, the external aqueous phase also contains stabilizers that stabilize the emulsion/slurry to prevent segregation of the internal non-aqueous (oily) phase and the external aqueous phase. The preferred stabilizers for preparing the isocyanate-based microcapsules according to the present invention are mainly acrylic copolymers that have sulfonate groups. Also suitable are copolymers of acrylamides and acrylic acid, copolymers of alkyl acrylates and N-vinylpyrrolidone, such as LUVISKOL® K15, K30 or K90 (BASF); sodium polycarboxylates, sodium polystyrene sulfonates, vinyl and methyl vinyl ether-maleic anhydride copolymers as well as ethylene, isobutylene or styrene-maleic anhydride copolymers, microcrystalline cellulose, which is commercially available, for example, under the name VIVAPUR®, diutan gum, xanthan gum or carboxymethyl celluloses.

The amount of stabilizers used can be in the range from 0.01 to 10% by weight and in particular in the range from 0.1 to 3% by weight, in each case based on the external aqueous phase.

Optionally, emulsifiers, preferably O/W emulsifiers, are used in the process according to the invention to allow a homogeneous distribution of the oil droplets of the internal non-aqueous phase in the external aqueous phase and to stabilize the emulsion. The same applies to the mixing of solid, non-soluble active ingredients in the external aqueous phase in order to stabilize the suspension thus obtained.

Suitable emulsifiers include, for example, non-ionic surfactants from at least one of the following groups:

Addition products of 2 to 30 mol ethylene oxide and/or 0 to 5 mol propylene oxide to linear fatty alcohols containing 8 to 22 carbon atoms, to fatty acids containing 12 to 22 carbon atoms, to alkylphenols containing 8 to 15 carbon atoms in the alkyl group and to alkylamines containing 8 to 22 carbon atoms in the alkyl radical;

Alkyl and/or alkenyl oligoglycosides with 8 to 22 carbon atoms in the alk(en)yl radical and their ethoxylated analogs;

Addition products of 1 to 15 moles of ethylene oxide to castor oil and/or cured castor oil;

Addition products of 15 to 60 moles of ethylene oxide to castor oil and/or cured castor oil;

Partial esters of glycerol and/or sorbitan with unsaturated, linear or saturated, branched fatty acids containing 12 to 22 carbon atoms and/or hydroxycarboxylic acids containing 3 to 18 carbon atoms and their adducts with 1 to 30 moles of ethylene oxide;

Partial esters of polyglycerol (average degree of autocondensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside) and polyglucosides (e.g. cellulose) with saturated and/or unsaturated linear or branched fatty acids containing 12 to 22 carbon atoms and/or hydroxycarboxylic acids containing 3 to 18 carbon atoms as well as their adducts with 1 to 30 mol ethylene oxide, preferably Cremophor®;

Mixed esters of pentaerythritol, fatty acids, citric acid and fatty alcohol and/or mixed esters of fatty acids with 6 to 22 carbon atoms, methylglucose and polyols, preferably glycerol or polyglycerol;

Mono-, di- and trialkyl phosphates as well as mono-, di- and/or tri-PEG-alkyl phosphates and their salts;

Wool wax alcohols;

Polysiloxane-polyalkyl-polyether copolymers or corresponding derivatives; block copolymers, e.g. polyethylene glycol-30 dipolyhydroxystearates; polymer emulsifiers, e.g. Pemulen grades (TR-1,TR-2) from Goodrich or Cosmedia® SP from Cognis;

polyalkylene glycols and glycerol carbonate.

Typical anionic emulsifiers that can be used in the process of the invention to produce the isocyanate-based microcapsules are aliphatic fatty acids with 12 to 22 carbon atoms, such as palmitic acid, stearic acid or behenic acid, and dicarboxylic acids with 12 to 22 carbon atoms, such as azelaic acid or sebacic acid.

Furthermore, zwitterionic surfactants can be used as emulsifiers in the process of the invention for the production of the isocyanate-based microcapsules. The term zwitterionic surfactants is used to describe surface-active compounds which carry in the molecule at least one quaternary ammonium group and at least one carboxylate and one sulfonate group. Particularly suitable zwitterionic surfactants are the so-called betaines such as the N-alkyl-N,N-dimethylammonium glycinates, for example the coco alkyl dimethylammonium glycinate, N-acylaminopropyl-N,N-dimethylammonium glycinate, for example the coco acylaminopropyl dimethylammoniumglycinate, and 2-alkyl-3-carboxylmethyl-3-hydroxyethylimidazolines each having 8 to 18 C atoms in the alkyl or acyl group, as well as the coco acylamino ethylhydroxyethyl carboxymethylglycinate. The fatty acid amide derivative known under the CTFA designation cocamidopropyl betaine is particularly preferred. Also, suitable emulsifiers are ampholytic surfactants. Ampholytic surfactants are surface-active compounds which, in addition to a C8/18 alkyl or acyl group in the molecule, contain at least one free amino group and at least one —COOH or —SO3H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Particularly preferred ampholytic surfactants are N-cocosalkylaminopropionate, cocosacylaminoethylaminopropionate and C12/18-acylsarcosine. Finally, cationic surfactants are also suitable as emulsifiers, with those of the esterquat type, preferably methyl-quaternized difatty acid triethanolamine ester salts, being particularly preferred.

The emulsifiers may be added to the external aqueous phase in an amount of from about 0.5% to about 10% by weight, and preferably from about 1% to about 5% by weight, each based on the total weight of the external aqueous phase.

The process according to the invention for producing the microcapsule dispersion can be carried out, for example, using the "inline" technique. In this process, the internal non-aqueous phase and the external aqueous phase are first fed separately to an emulsifying turbine by means of a forced metering pump, and are combined shortly before entering the emulsifying turbine or are combined in the emulsifying turbine, at a throughput volume of 1200 to 1500 l/h.

The weight ratio of internal non-aqueous phase to external aqueous phase is preferably in a range from 10:90 to 60:40, preferably in a range from 30:70 to 50:50.

In addition, the process according to the invention for producing the isocyanate-based microcapsules can also be carried out in conventional dispersion apparatus or emulsification apparatus.

The process of emulsification or suspension in the method according to the invention is advantageously carried out for a time of from 0.5 to 10 minutes, preferably from 0.75 to 4 minutes and most preferably from 1 to 2.5 minutes, until a capsule size of from 10 to 50 µm±5 µm has been achieved.

In a subsequent step of the process according to the invention, a first crosslinking of the material of the capsule shell or capsule wall is also carried out by stirring at a stirring speed of 1000 to 1500 rpm, preferably at a stirring speed of 1200 rpm. The first crosslinking is performed by adding an amine that reacts at an acidic pH to crosslink and stabilize the capsule shell enclosing the core material.

Particularly advantageous results for capsule shell formation are obtained when the first crosslinking with the amine occurs at an acidic pH of 2 to 7, preferably occurs at a pH of 2 to 6, and most preferably occurs at a slightly acidic pH of 3 to 5. For this purpose, an acid, for example formic acid or acetic acid, is added to the external aqueous phase and a pH in the above ranges is adjusted.

Carrying out the first crosslinking in an acidic pH range has the advantage over crosslinking in a basic environment that the hydrophobic active ingredients with aldehyde, carboxylic acid or ester functionalities do not saponify during the first reaction steps of crosslinking the isocyanate or isothiocyanate.

This prevents the active ingredient(s) to be encapsulated, for example a perfume oil, from being chemically altered, resulting in a loss of the active ingredients on the one hand and the emulsion becoming unstable on the other.

Even more preferably, the first crosslinking step is performed at a temperature of 20° C. to 30° C.

The amine reacting at an acidic pH is selected from the group consisting of basic amino acids and their hydrochlorides, in particular lysine hydrochloride or ornithine hydrochloride. Most preferred as crosslinking agent is lysine hydrochloride.

The first crosslinking agent is added to the emulsion either as such, for example as a solid, or in the form of an aqueous solution.

The first crosslinking agent is present in the aqueous solution at a concentration of 0.5 to 2 mol/l, preferably 1 mol/l. The solution has a pH value of 4 to 7.

The first crosslinking in the process according to the invention is carried out for a period of about 10 minutes to 20 minutes, preferably for a period of 12 to 18 minutes and most preferably for a period of about 15 minutes.

The first crosslinking step is followed by a further crosslinking step of the material of the capsule shell or capsule wall by adding an amine that reacts at an alkaline pH to form a polyurea matrix.

Particularly advantageous results for capsule formation were obtained when further crosslinking with the amine reacting at an alkaline pH occurs at an alkaline pH of 7 to 14, preferably at an alkaline pH of 7 to 10 and most preferably at an alkaline pH of 7 to 8.

Even more preferably, the step of further crosslinking is carried out at a temperature of 35° C. to 50° C.

The amine reacting at an alkaline pH is selected from the group consisting of the di-, tri- and polyamines and guanidinium carbonate. Most preferred is guanidinium carbonate as another crosslinking agent.

The further crosslinking agent is added to the emulsion either as such, for example as a solid, or in the form of an aqueous solution.

The further crosslinking agent is present in the aqueous solution in a concentration of 0.5 to 2 mol/l, preferably of 1 mol/l. The solution has a pH of 7 to 14, preferably a pH of 12.

By adding the amine, which reacts at an alkaline pH, the pH of the emulsion is shifted to higher pH values. The pH of the final product, i.e. the final capsule slurry, is 5 to 8, preferably a pH of 6 to 7.

An essential feature of the production of isocyanate-based microcapsules according to the present invention is thus that the first crosslinking is carried out at an acidic pH and the subsequent further crosslinking is carried out at an alkaline pH.

Due to the pH gradient, a capsule shell with a linear polyurea matrix is initially formed during the first crosslinking, preferably at an acidic pH. During subsequent further crosslinking, preferably at a basic pH, the capsule shell is further crosslinked and a spatially crosslinked polyurea matrix is formed.

During the two crosslinking steps, the stirring power is reduced, for example to a stirring speed of about 800 to 1200 rpm, in order not to break the forming microcapsules again immediately.

After complete crosslinking and formation of the capsule shell or capsule wall, the capsules produced by the process of the invention are present as crude microcapsules in the form of an aqueous dispersion or slurry.

After crosslinking, the microcapsules in the slurry still have a flexible shell, which is not particularly stable and therefore breaks open easily. For this purpose, hardening of the shell is carried out. Hardening is triggered by a change in temperature by gradually raising the slurry to a temperature of 70° C., preferably to a temperature in the range of 60 to 65° C. The curing is usually carried out over a period of 2 to 4 hours.

In addition, it is advantageous to add substances to the external aqueous phase for hardening. For this purpose, natural plant tannins of the tannin type are used, which, from a chemical point of view, are proanthocyanidins as found in dicotyledonous shrubs, bushes and leaves, especially in the tropics and subtropics. The terpenes generally have molecular weights in the range of 500 to 3,000 KDa. A preferred example of a suitable tannin is corigallin. For curing, an aqueous preparation of the tannins is added to the aqueous dispersion containing the crude microcapsules. Typically, the tannins are added in amounts of from about 0.1% to about 2% by weight, and preferably from about 0.5% to about 1.5% by weight, based on the microcapsules.

An important criterion for the usability of microcapsules is the weight ratio of core material to capsule wall material. While on the one hand the aim is to achieve the highest possible proportion of core material to enable the capsules to have the highest possible utility value, on the other hand it is necessary for the capsules to still have a sufficient proportion of capsule wall material to ensure the stability of the capsules.

According to the invention, it has been found to be particularly advantageous that the microcapsules are designed in such a way that the microcapsules have a weight ratio of core material to capsule wall material which is from 50:50 to 90:10, preferably from 70:30 to 80:20.

After curing, the microcapsules produced by the process according to the invention are present as a dispersion in water, which is also referred to as a microcapsule dispersion.

In this form, the microcapsules are basically ready for sale; however, it is recommended to dry them for preservation purposes.

In principle, processes such as lyophilization can be used for this, but spray drying, for example in the fluid bed, is preferred. It has proved advantageous to add further polysaccharides, preferably dextrins and in particular maltodextrins, to the dispersion at temperatures of about 20 to about 50° C. and preferably about 40° C., which support the drying process and protect the capsules during this process. The amount of polysaccharides used may be from about 50 to about 150% by weight, and preferably from about 80 to about 120% by weight, based on the capsule mass in the dispersion.

The spray drying itself can be carried out continuously or in batches in conventional spray systems, with an inlet temperature of about 170 to about 200° C. and preferably about 180 to 185° C., and an outlet temperature of about 70 to about 80° C. and preferably about 72 to 78° C.

It has been shown that the process according to the invention can be used to encapsulate hydrophobic active ingredients, in particular hydrophobic active ingredients that exhibit aldehyde, carboxylic acid or ester functionality. The microcapsules are characterized by excellent stability and release capacity.

Surprisingly, it has been found that the process according to the invention can furthermore be used to produce microcapsules with a reduced amount of material of the capsule shell or capsule wall by up to 50% without any loss or degradation of the stability of the microcapsules obtained, as shown in the following embodiments. As a result, microcapsules can be produced with a reduced amount of starting substance isocyanate while maintaining the same amount of active ingredient to be encapsulated.

In addition, the microcapsules produced by the process of the invention are formaldehyde-free.

In another aspect, the present invention relates to microcapsules produced according to the process of the invention.

As can be seen from the data below, emulsification in the presence of a protective colloid and a catalyst and two-step crosslinking of the isocyanate-based shell material with an amine reactive at an acidic pH and with an amine reactive at an alkaline pH produces stable microcapsules. In particular, stable microcapsules are formed with a core material that has a high proportion of active ingredients with aldehyde, carboxylic acid or ester functionality.

The microcapsules according to the invention are illustrated in FIG. 1 at 10× magnification. The structure of the capsule shell can be observed by optical microscopy. While oil droplets are visible at the beginning of the manufacturing process, dented microcapsules can be seen after crosslinking, heating and cooling.

The microcapsules produced by the process according to the invention can be characterized by the following parameters of their size distribution:
  d(0.1) value: 10% of the capsules are smaller than this value;
  d(0.5) value: 50% of the capsules are larger, 50% of the capsules are smaller than this value; and
  d(0.9) value: 10% of the capsules are larger than this value.

To determine the particle size, the microcapsules of the invention are dispersed in water as part of a dynamic process and the particle size is then determined by laser diffraction. Depending on the size of the capsule, the laser beam is refracted differently and can thus be converted to a size. The Mie theory was used for this purpose. A MALVERN Mastersizer 3000 was used for the particle measurement.

Figure 2:
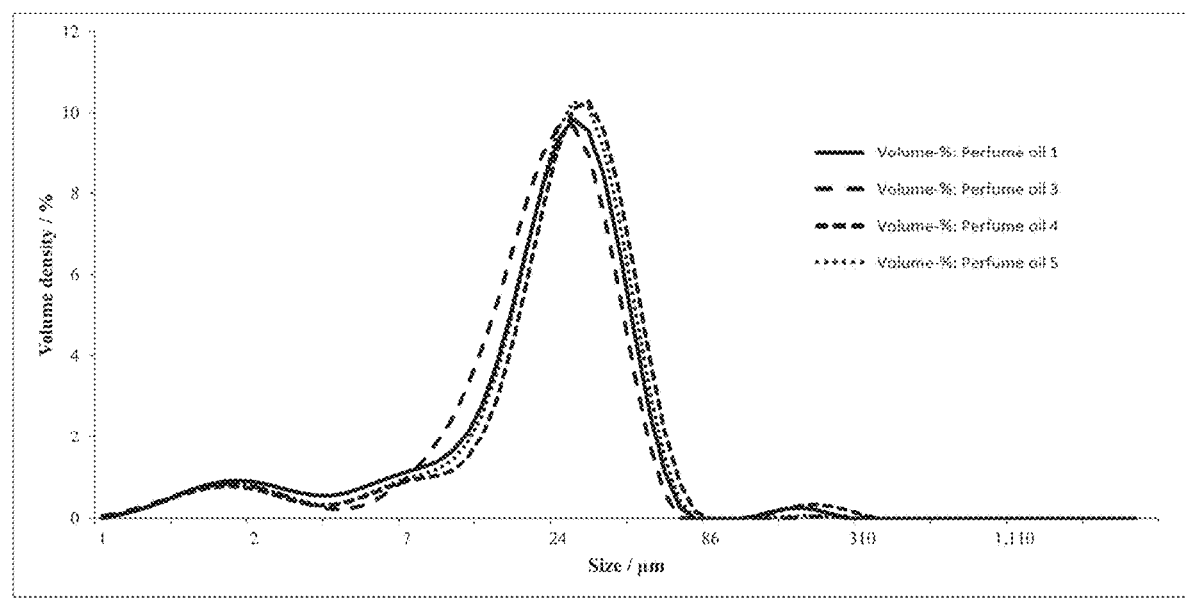
FIG. 2 is a diagram showing the particle size distribution (d(0.5) value) of microcapsules containing different perfume oils according to the invention.

The microcapsules according to the invention are characterized in that they have a particle size distribution at a d(0.5) value of 10-50 µm, preferably a d(0.5) value of 20 to 30 µm, as illustrated in FIG. 2, and a particle size distribution at a d(0.9) value of 10 to 120 µm, preferably a d(0.9) value of 60 to 90 µm.

Figure 3:
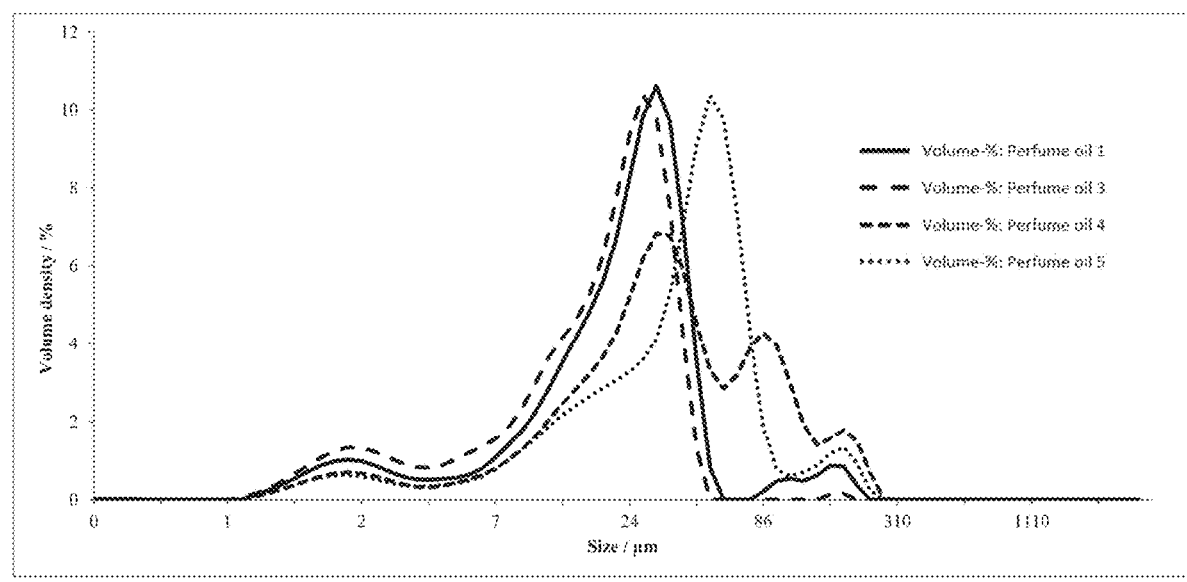
FIG. 3 is a diagram showing the particle size distribution (d(0.5) value) of prior art microcapsules with different perfume oils.

FIG. 3 shows the particle size distribution (d(0.5) value) of prior art microcapsules. For perfume oils 4 and 5, it is noticeable that size adjustment was not possible.

Figure 4:
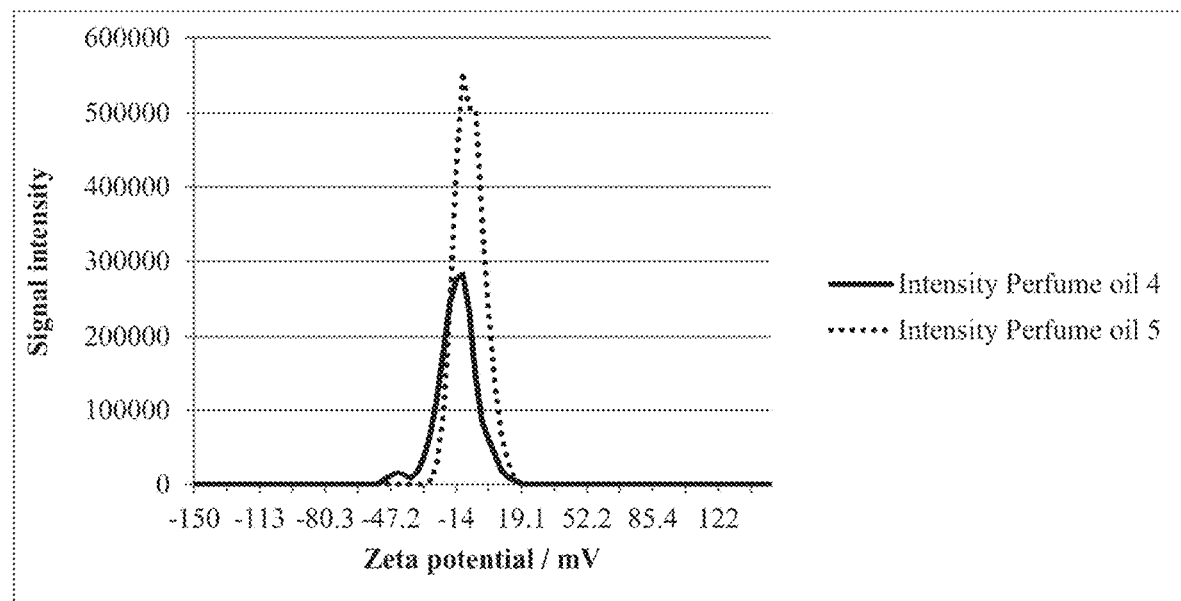
FIG. 4 is a diagram showing the zeta potential of microcapsules containing perfume oil 4 or 5 according to the invention.
Figure 5:
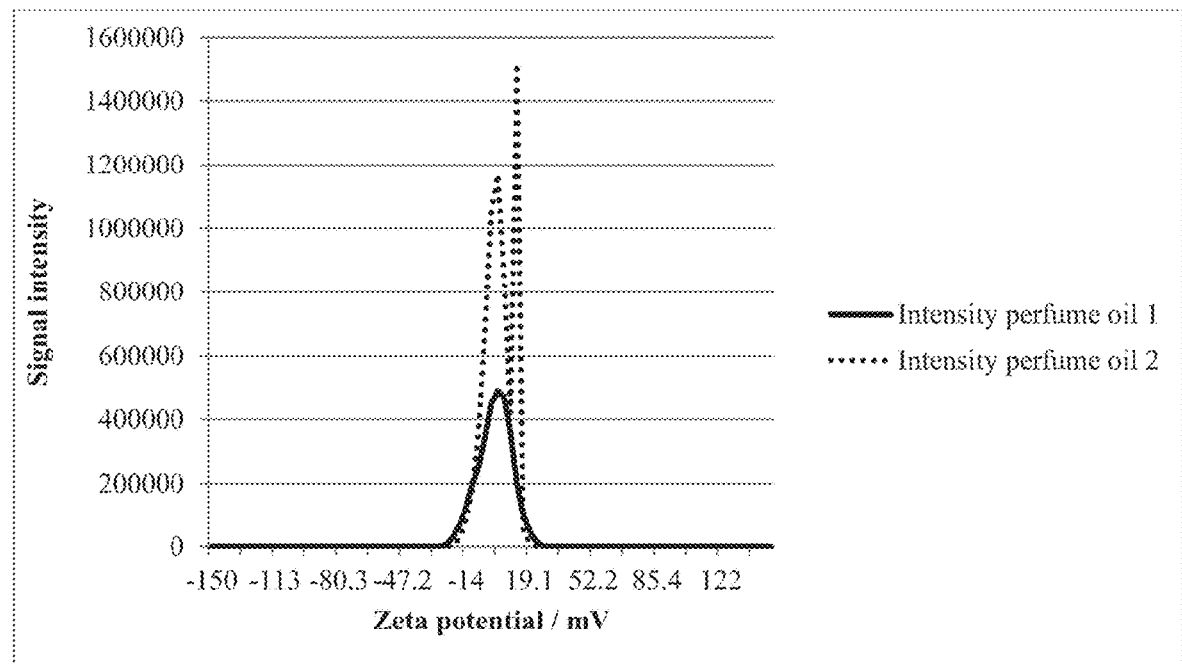
FIG. 5 is a diagram showing the zeta potential of prior art microcapsules containing perfume oil 1 or 2.

The microcapsules produced by the process according to the invention are further characterized by having a zeta potential which is characteristically −5 to −15 mV for the microcapsules according to the invention, as illustrated in FIGS. 4 and 5. Preferably, the zeta potential is −10 mV. Each microcapsule has a zeta potential. The zeta potential is independent of the active ingredient to be encapsulated, in particular the perfume oil, but nevertheless depends on the polymer of the capsule shell. Due to the change in the zeta potential during the production of the microcapsules according to the invention, it is possible to prove that a new polymer or shell has been formed, since the surface and thus also the surface charge (zeta potential) of the particles in the emulsion change. The microcapsules according to the invention, which are produced without a catalyst, have a zeta potential of −27 mV. Prior art microcapsules have a zeta potential of ±0 mV. In the context of the measurements, the Smoluchowski theory was applied. A MALVERN Zetasizer nano ZS was used to measure the zeta potential.

Regardless of the signal intensity, which comes from dosing the microcapsules in the dispersing medium, it is clear from FIGS. 4 and 5 that the zeta potential for the microcapsules according to the invention is −5 to 0 mV, since the use of the catalyst and the accompanying acceleration of the polyurethane formation reaction are characteristic of the deviating zeta potential of −27 mV.

Accordingly, another aspect of the present invention is microcapsules which comprise or consist of:
  a core comprising or consisting of at least one hydrophobic agent; and
  a capsule shell comprising an isocyanate having two or more isocyanate groups which is crosslinked in the presence of a protective colloid and a catalyst in a first step by an amine reacting at an acidic pH and in a further step by an amine reacting at an alkaline pH.

Surprisingly, it was found that the microcapsules produced by the process of the invention have a layered shell structure or multilayer capsule shell or capsule wall formed of a first layer of polyurethane near the core of the microcapsule and a second layer of polyurea at the outer edge of the microcapsule.

In a preferred variant, therefore, the present invention relates to isocyanate-based microcapsules characterized in that the capsule shell comprises or consists of: a first layer of polyurethane and a second layer of polyurea.

Due to the excellent stability and an outstanding release capacity of the microcapsules and the possibility of encapsulating a wide range of hydrophobic active ingredients with the microcapsules according to the invention, the isocyanate-based microcapsules according to the present invention can be used for a wide range of applications for fragrancing and flavoring.

Thus, in a further aspect, the present invention ultimately relates to the use of the microcapsules according to the invention or suspensions comprising the microcapsules according to the invention for the production of detergents, fabric softeners, cleaning agents, scent boosters (fragrance enhancers) in liquid or solid form, cosmetics, personal care products, agricultural products or pharmaceutical products.

A particularly suitable form of use of the microcapsules according to the invention is to add them to the final product in the form of a suspension. Therefore, the present invention also relates to a suspension of the microcapsules described above in a liquid, in particular in water. Such a suspension exhibits particularly advantageous properties if it is designed such that the proportion by weight of the microcapsules is about 20 to 60% by weight, in particular about 25 to 50% by weight, more preferably about 30 to 35% by weight.

To prevent segregation of such a suspension and thus achieve high storage stability, it has proved advantageous for the suspension to have a viscosity of 12 to 1500 mPas. To obtain the desired viscosity of the suspension, a thickening agent is preferably used.

The microcapsules according to the invention are particularly suitable for the inclusion of hydrophobic fragrances or aromatic substances, which can then be used in various cleaning products.

The present invention thus also relates in particular to the use of the microcapsules described as a component of laundry detergents, in particular liquid laundry detergents, fabric softeners, cleaning agents, scent boosters (fragrance enhancers) in liquid or solid form, cosmetics, personal care products, in particular shower gels, shampoos, deodorants and/or body lotions.

The proportion of microcapsules in the aforementioned products is from 0.05 to 15% by weight, based on the total weight of the product, preferably from 0.2 to 5% by weight.

WORKING EXAMPLES

The microcapsules of the present invention and their advantageous properties are described in more detail with reference to the following examples.

The stability tests listed below were carried out at 50° C.

Example 1

Stability data of microcapsules prepared according to the method of the invention with and without catalyst (DABCO), a first crosslinker (lysine hydrochloride) at 20 to 30° C. and another crosslinker (guanidinium carbonate) at 35 to 50° C. Polyvinyl alcohol was used as protective colloid.

The stability test was performed using a representative softener (fabric softener) into which the microcapsules were incorporated in an amount of 1% by weight. The softener was then stored for the periods mentioned below.

The capsule contents were analyzed by GC/MS (gas chromatography and mass spectrometry). The perfume oil content in the capsules was determined by comparison measurement with a standard. A result of, for example, 64% means that 36% of the amount of perfume oil originally used is no longer in the capsule.

TABLE 1

| Perfume oil | 3 days without catalyst | 10 days without catalyst | 3 days with catalyst | 10 days with catalyst |
| --- | --- | --- | --- | --- |
| Perfume oil 1 TomCap (20% substance) | 64% | 57% | 70% | 61% |

TABLE 1-continued

| Perfume oil | 3 days without catalyst | 10 days without catalyst | 3 days with catalyst | 10 days with catalyst |
| --- | --- | --- | --- | --- |
| Perfume oil 2 November 15 (15% substance) | 71% | 63% | 73% | 64% |
| Perfume oil 3 Extreme Power Safe (25% substance) | 81% | 73% | 91% | 85% |
| Perfume oil 4 Wonderball (30% substance) | 29% | — | 77% | 69% |
| Perfume oil 5 High ball (50% substance) | 10% | — | 86% | 78% |
| Perfume oil 6 King of Cool (45% substance) | 21% | — | 63% | 49% |

Note:
Substance: proportion of aldehyde, carboxylic acid, ester, primary alcohol components in perfume oil composition.

Perfume oils 4 to 6 are characterized by a high proportion of components with ester, aldehyde and carboxylic acid functionality. With the method according to the invention, excellent stability data are also obtained for such perfume oils.

Example 2

Stability data of microcapsules prepared by the method of the invention with different protective colloids: Crosslinking with lysine hydrochloride at a pH of 5.0; encapsulated oil: caren delta-3 nat, caryophyllen nat. rect., phellandrene I, pinene alpha laevo nat., terpinene gamma, verdoracine.

TABLE 2

| Protective colloid | 3 days | 10 days |
| --- | --- | --- |
| Polyvinyl alcohol | 83% | 72% |
| Cationic ammonium derivative of PVOH | 69% | 54% |
| Strength | 80% | 75% |

All microcapsules show excellent stability data. When the ammonium derivative of PVOH is used, the stability is slightly lower, which is due to the reduced number of hydroxyl groups.

Example 3

In the example of perfume oil 4, an shell reduction was carried out. The content of monomer (isocyanate) in the internal non-aqueous phase was reduced.

TABLE 3

| Monomer to oil ratio | 3 days | 10 days |
| --- | --- | --- |
| 1:20 | 77% | 69% |
| 1:30 | 78% | 70% |
| 1:33 | 70% | 62% |
| 1:35 | 66% | 58% |
| 1:40 | 70% | 59% |

Note:
A ratio of 1:20 means that 5 g of monomer were used to encapsulate 100 g of perfume oil Capsules with a residual oil content of >40% after 10 days are considered stable; in this case, the shell can be reduced by 50%.

Example 4

Comparison of the stability of microcapsules produced by the prior art encapsulation technology and by the method according to the invention.

The microcapsules were prepared as follows:

Prior art encapsulation technology: crosslinking: polyurea network only; catalyst: none; protective colloid: polyvinyl alcohol; pH: 9.

Process according to the invention: non-aqueous phase of two isocyanates dissolved in perfume oil plus solvent; aqueous phase of polyvinyl alcohol and DABCO; emulsification process: addition of lysine hydrochloride reacting in the acidic pH range (pH: 4 to 7); addition of guanidinium carbonate reacting in the alkaline pH range (pH: 7 to 14); pH of final capsule slurry: 5 to 8.

TABLE 4

| Perfume oil | 3 days Technology state of the art | 10 days Technology state of the art | 3 days Technology according to the invention | 10 days Technology according to the invention |
|---|---|---|---|---|
| Perfume oil 1 TomCap (20% substance) | 77% | 70% | 70% | 61% |
| Perfume oil 2 November 15 (15% substance) | 90% | 85% | 73% | 64% |
| Perfume oil 3 Extreme Power Safe (25% substance) | 94% | 92% | 91% | 85% |
| Perfume oil 4 Wonderball (30% substance) | 48% | 28% | 77% | 69% |
| Perfume oil 5 High ball (50% substance) | 20% | — | 86% | 78% |
| Perfume oil 6 King of Cool (45% substance) | 35% | 30% | 63% | 49% |

Note:
Substance: proportion of aldehyde, carboxylic acid, ester, primary alcohol components in perfume oil composition.

Compared to the prior art encapsulation technology, the encapsulation technology according to the invention is universally applicable, while the prior art technology shows a strong drop in stability for perfume oils with a high proportion of components with ester, aldehyde and carboxylic acid functionality. The encapsulation technology according to the invention shows gains in stability, especially for perfume oils 4 to 6, while the stabilities for perfume oils 1 to 3 are slightly lower.

Example 5: Formation of a Multilayer of the Capsule Shell

TABLE 5

| Protective colloid | 3 days 50° C. | 10 days 50° C. |
|---|---|---|
| State of the art capsule | 77% | 70% |
| Capsule with PVOH according to the invention | 70% | 61% |
| Capsule according to the invention with ammonium derivative of PVOH | 41% | 33% |
| Capsule according to the invention containing ammonium derivative of PVOH and glycerol. | 55% | 49% |
| Modified starch capsule according to the invention | 76% | 67% |

By using various protective colloids, it could be demonstrated that a multilayer capsule shell or capsule wall is formed with the process according to the invention. While the ammonium derivative of polyvinyl alcohol (PVOH) was used as the protective colloid in the process without the addition of further hydroxyl groups, the capsule stability was significantly lower than when glycerol was additionally added in the process, whereby an increase in the stability of the microcapsules was observed. By selectively omitting hydroxyl groups (see "capsule according to the invention with ammonium derivative of PVOH") and selectively adding hydroxyl groups (see "capsule according to the invention with ammonium derivative of PVOH and glycerol"), the formation of a polyurethane layer can be demonstrated, which massively increases the stability.

Example 6: Sensory Evaluation of the Microcapsules According to the Invention

Sensory evaluation of the microcapsules was performed as follows: The microcapsules, as listed in FIG. 6, were incorporated into a fabric softener and then washed. The sensory odor test was carried out on mixed fiber cloths made of cotton and polyester.

State of the art capsule: 10 days, 50° C., 28% perfume oil.
Capsule with reduced shell according to the invention: 10 days, 50° C., 59% perfume oil.

The 24 test subjects rated the fragrance intensity of the mixed fiber cloths after washing on a scale of 1 (no odor) to 9 (very strong odor).

The microcapsules according to the invention have practically the same odor as the microcapsules of the prior art. The advantage here lies in the stability of the microcapsules according to the invention. Despite polymer reduction from 1:20 to 1:40, based on the perfume oil, these have a higher stability.

Due to the advantageous properties described above, a consistent quality and consequently sensory stability can be expected in the long term with the microcapsules according to the invention compared to the microcapsules from the prior art. The microcapsules from the prior art are just as good as the microcapsules according to the invention immediately after their production. Over time, however, they lose oil more quickly and thus have a less intense odor than the microcapsules according to the invention.

The invention claimed is:

1. A process for preparing isocyanate-based microcapsules comprising:
   (a) providing an internal non-aqueous phase comprising at least one isocyanate having two or more isocyanate groups or at least one isothiocyanate having two or more isothiocyanate groups and a hydrophobic agent to be encapsulated;
   (b) providing an external aqueous phase comprising at least one protective colloid and a catalyst;
   (c) mixing the internal non-aqueous phase and the external aqueous phase, optionally in the presence of a stabilizer and/or an emulsifier, to obtain an oil-in-water emulsion;
   (d) a first crosslinking by addition to the composition of step (c) of an amine reacting at an acidic pH;
   (e) further crosslinking by addition to the composition of step (d) of an amine reacting at an alkaline pH to obtain microcapsules;
   (f) curing the microcapsules obtained in step (e); and optionally:
   (g) separating the microcapsules from the reaction solution and further optionally drying of the microcapsules.

2. The process according to claim 1, wherein the isocyanate having two or more isocyanate groups or the isothiocyanate having two or more isothiocyanate groups is selected from the group consisting of aliphatic, cycloaliphatic, hydroaromatic, aromatic or heterocyclic polyisocyanates or polyisothiocyanates, their substitution products and mixtures of the aforementioned compounds.

3. The process according to claim 1, wherein the hydrophobic agent to be encapsulated is selected from one or more in the group of fragrances, aromatic substances, biocides, insecticides, a substance from the group of repellents, food additives, cosmetic active ingredients, pharmaceutical active ingredients, agrochemicals, dyes, luminous dyes, optical brighteners, solvents, waxes, silicone oils, lubricants.

4. The process of claim 1, wherein the hydrophobic agent to be encapsulated is selected from one or more in the group of fragrances or flavoring agents having aldehyde, carboxylic acid or ester functionality.

5. The process according to claim 1, wherein the at least one protective colloid is selected from one or more in the group of diols, ethanediol, 1,2-propanediol, 1,3-propanediol, 1,2-butanediol, isomeric butanediol, 1,2-pentanediol, 1,2-hexanediol, 1,2-octanediol, 1,2-decanediol, 1,2-dodecanediol, polyols, triols, glycerol, ethoxylation products of glycerol, propoxylation products of glycerol, trimethylolpropane, ethoxylation products of trimethylolpropane, propoxylation products of trimethylolpropane, polyvinyl alcohol (PVOH), derivatives of PVOH, ammonium- or sulfonate-functionalized polyvinyl alcohols, polyphenols, 1,3,5-trihydroxybenzene, starch, chemically, mechanically and/or enzymatically modified starch, carboxymethylcellulose, and polyvinylpyrrolidone.

6. The process claim 1, wherein the at least one protective colloid is used in combination with starch.

7. The process of claim 1, wherein the catalyst is diazobicyclo[2.2.2]octane.

8. The process of claim 1, wherein the first crosslinking by the amine reacting at an acidic pH occurs at a pH in a range of 2 to 7 and optionally at a temperature in a range of 20° C. to 30° C.

9. The process of claim 1, wherein the amine reacting at an acidic pH is selected from one or more in the group of acidic amino acid hydrochlorides, lysine hydrochloride, and ornithine hydrochloride.

10. The process according to claim 1, wherein the further crosslinking by the amine reacting at an alkaline pH is carried out at a pH in a range of 7 to 14 and optionally at a temperature in a range of 35° C. to 50° C.

11. The process of claim 1, wherein the amine reacting at an alkaline pH is selected from one or more in the group of the di-, tri- and polyamines and guanidinium carbonate.

12. The process of claim 1, wherein the curing of the microcapsules in step (f) is carried out at a temperature up to 70° C.

13. Microcapsules obtained according to claim 1.

14. Isocyanate-based microcapsules comprising:
   a core comprising at least one hydrophobic agent; and
   a capsule shell comprising an isocyanate having two or more isocyanate groups which is crosslinked in the presence of a protective colloid and a catalyst in a first step by an amine reacting at an acidic pH and in a further step by an amine reacting at an alkaline pH.

15. The isocyanate-based microcapsules of claim 14, wherein the capsule shell comprises: a first layer of polyurethane; and a second layer of polyurea.

16. A method of using the microcapsules according to claim 15 for the manufacture of one or more products in the group of detergents, fabric softeners, cleaning agents, scent boosters in liquid or solid form, cosmetics, personal care products, agricultural products, and pharmaceutical products.

17. The method of claim 16, wherein the microcapsules are in suspension form.

18. The microcapsules of claim 14, consisting of the core comprising at least one hydrophobic agent; and the capsule shell comprising an isocyanate having two or more isocyanate groups which is crosslinked in the presence of a protective colloid and a catalyst in a first step by an amine reacting at an acidic pH and in a further step by an amine reacting at an alkaline pH.

19. The microcapsules of claim 18, wherein the capsule shell consists of a first layer of polyurethane and a second layer of polyurea.

20. The microcapsules of claim 15, wherein the capsule shell consists of a first layer of polyurethane and a second layer of polyurea.

* * * * *